United States Patent [19]

Cushman

[11] 4,304,998
[45] Dec. 8, 1981

[54] PANORAMIC DENTAL X-RAY MACHINE EMPLOYING IMAGE INTENSIFYING MEANS

[75] Inventor: Robert H. Cushman, Princeton, N.J.

[73] Assignee: Pennwalt Corporation, Philadelphia, Pa.

[21] Appl. No.: 53,127

[22] Filed: Jun. 28, 1979

Related U.S. Application Data

[63] Continuation-in-part of Ser. No. 926,175, Jul. 20, 1978, abandoned.

[51] Int. Cl.$^3$ .............................................. G03B 41/16
[52] U.S. Cl. .......................... 250/439 P; 250/213 VT
[58] Field of Search ...................... 250/439 P, 213 VT

[56] References Cited

U.S. PATENT DOCUMENTS

| | | | |
|---|---|---|---|
| 2,798,958 | 7/1957 | Hudson | 250/439 P |
| 3,681,606 | 8/1972 | Tinney | 250/213 VT |
| 4,140,900 | 2/1979 | Wang | 250/213 VT |
| 4,228,356 | 10/1980 | Cushman | 250/439 P |

*Primary Examiner*—Craig E. Church

[57] ABSTRACT

Panoramic dental X-ray machine includes a tubehead-camera assembly employing a suitable type image intensifier having a radiation input face of substantially similar shape and dimensions as a slot in a front panel of the camera assembly, the input face being secured against the slot and aligned therewith such that radiations passing through the slot must then pass through the image intensifier. A fast light-sensitive film constantly delicately presses against an output face of a fiber optic plate associated with the image intensifier as the film travels across the output face at a rate of speed dictated by the type radiographic image desired, i.e., continuous, discontinuous, or by the shape of the curved plane in focus. The image intensifier eliminates the need for conventional intensifying screens associated with panoramic dental radiographic systems. Resultant radiographs possess good contrast and resolution and are produced full size without the need of any peripheral electronic components. Invention greatly reduces the kVp and/or milliamperes required to power the tubehead as well as minimizing radiation dosages to the patient.

8 Claims, 4 Drawing Figures

PANORAMIC DENTAL X-RAY MACHINE EMPLOYING IMAGE INTENSIFYING MEANS

The present application is a continuation-in-part of my copending application Ser. No. 926,175, filed July 20, 1978, now abandoned, same title, and assigned to the assignee hereof.

STATEMENT OF THE INVENTION

The present invention relates to X-ray machines and more particularly to improved means for obtaining panoramic radiographs of dental arch areas.

CROSS-REFERENCE TO OTHER RELATED APPLICATIONS

Reference is hereby made to the following copending application
(a) Ser. No. 889,708, filed Mar. 24, 1978, for "Film Drive Mechanism for Panoramic Dental X-Ray Machine", of Anthony Ciavattoni et al., assigned, now to U.S. Pat. No. 4,172,977 to the present assignee.

BACKGROUND OF THE INVENTION

Prior art panoramic dental X-ray machines are well known. Some provide a continuous image of the dental arch area and commonly employ an X-ray source and X-ray film both optically aligned with each other and supported on a rotatable carrying arm which orbits a patient situated in the path of the X-ray beams. The patient may remain stationary or be transported in a patient chair in accordance with various type drive mechanisms in order to simulate the generally elliptical shape of the human dental arch. The continuous image radiograph provides the dentist with a panoramic view of the teeth and associated structures and is therefore a useful diagnostic aid in many phases of dental practice.

Various other prior art apparatus provide a discontinuous, or split image panoramic radiograph which possesses certain advantages. Here, the dentist is presented with additional interpretive information since two distinctly different views of the incisors, or centrals area are provided. Additionally, overlying spinal shadows which would be cast over the central-bicuspid region are eliminated since X-rays are not generated when the spine is aligned with the X-ray source and film.

Regardless of the type radiographic image to be obtained, i.e., continuous or discontinuous, compensation is usually made for the fact that the curvature of the desired area of focus is generally not a true circle or ellipse. Thus, the rate of film travel must be varied in accordance with the rate of travel of the X-ray source about the patient's head in order that the radiological projections occupy a distance on the film commensurate with the linear distance of a curved structure being X-rayed, such as a typical dental arch.

In U.S. Pat. No. 2,798,958, apparatus is disclosed for varying the rate of film travel relative to the rate of travel of the X-ray source. The X-ray source and film carrier are both supported by a single member permitting both the X-ray source and film carrier to orbit the patient at an uniform rate of travel. Means are also disclosed for reorienting the patient after comletion of one-half of the excursion cycle in order to relocate the center of the axis of rotation with respect to the patient's head prior to X-raying the other one-half of the dental arch in order to provide the discontinuous, or split radiographic images.

In U.S. Pat. No. 3,045,118, apparatus is disclosed which automatically shifts the patient in order that the line of sight between the X-ray source and film bypasses the patient's spinal column and permits X-raying of the other half of the dental arch. Apparatus is also disclosed therein for continuously moving an X-ray source and extra-oral film holder about the patient.

In U.S. Pat. No. 3,636,349, structure is disclosed for revolving the X-ray source and film carrier about the head of a patient who remains fixed in position while the centerline of the orbit continuously moves through an arcuate path approximating the arch of the patient's teeth. The patent further discloses film carrier means which may be used advantageously in the practice of the present invention.

In U.S. Pat. No. 4,125,774, improved X-Y drive mechanism permits both continuous and discontinuous radiographic images of the dental arch area to be accurately portrayed.

Thus, the prior art discloses various types of structures, apparatus and mechanisms for orbiting the X-ray source-X-ray film (tubehead-camera) assemblies in circular or arcuate paths; for varying film-travel speed in accordance with tubehead-camera assembly movements; for shifting the patient in a chair; and for providing continuous or discontinuous type radiographic images.

In each of the aforedescribed prior art systems, the patient is subjected to radiation doses of sufficiently high intensify in order to project the desired images adequately onto the X-ray film, necessitating a supply of considerable power to the X-ray source or tubehead. The resultant radiographs lacked good static and dynamic resolution, providing approximately 5 line pairs/mm for static applications and only 3 to 4 line pairs/mm for dynamic applications. Our laboratory tests have confirmed that the prior art intensifying screens limit the total system resolution and hence, when the screens are eliminated as in the present invention, higher resolutions are obtained as the film has much higher resolution capabilities. It is noted that the unaided human eye is capable of distinguishing resolutions approaching about 7 line pairs/mm.

Further, in each of the prior art systems abovementioned, the X-ray film is required to be sandwiched between conventional intensifying screens which permit the film to obtain the image in a shorter time and with less X-ray exposure to the patient. The screens and film move as a unit past the camera slot. These intensifying screens are expensive and reusable but are easily damaged. For example, cracks, fissures, and embedded dirt in the screens provide false images, as do bent screens; electrostatic charges which have developed on the screen surfaces create lightning-like patterns on the radiograph, and the like. To the best knowledge of the inventor, all current panoramic dental X-ray machines employ intensifying screens with the X-ray film.

Attempts have recently been made to employ image intensification devices in conjunction with associated electronic peripheral components and equipment to substantially lessen the overall radiation dosages to which a patient is subjected without any concomitant sacrifice in contrast, resolution, or physical dimensions of the final radiograph. It is appreciated that radiographs of adequate physcial dimensions are considered necessary if meaningful information therefrom is to be consistently obtained by a dentist.

In accordance with the above, radiation exiting the patient may be directed into a system of components including a suitable image intensifying device in order to provide a real-time oscilloscope display for subsequent photographing thereof. The image intensifiers so employed, in the main, were very expensive, and sufficiently large in order to produce a proportionally large real-time display, the radiograph of which would require no electronic or optical "blow-up". It should be appreciated that blown-up radiographs amplify the already rather poorly resolved image as well as introduce geometric distortions thereunto, both of which could lead to a faulty diagnosis. Additionally, the use of such prior art image intensifying devices generally required the presence of cathode ray tubes, electronic amplifiers and sweeps, synchronous circuits, and the like, the totality of which still yielded undesirably low resolution radiographs.

SUMMARY OF THE INVENTION

The present invention may be used advantageously with the abovediscussed patented prior art structures, apparatus, and mechanisms, or may be readily adapted thereto be one skilled in the art. Further, the present invention is amenable and compatible with panoramic or slit radiological techniques, and proposes an inexpensive, relatively uncomplicated system whereby the intelligence carrying radiations are directed into a suitable image intensifying device to provide a highly compact unit, the image intensifying device having an input face substantially identical in dimensions to the narrow slot opening of the camera, or film holder assembly, which carries the light sensitive film to be activated by the light exiting the output face of the image intensifying device. No intensifying screens are required to be employed with the X-ray film.

The active area of the image intensifying device will be elongated and rectangular in shape and will ideally possess a shallow depth, the entire device being readily attachable to the camera for optical alignment with the camera slot. The light sensitive film, without intensifying screens, may press delicately against the output face of a fiber optic face plate associated with the image intensifier or be in very close spaced relationship thereto as the film travels in accordance with a controlled rate of speed dictated by the type of image desired, as described in the aforementioned patents or cross-referenced copending application, or by the shape of focal trough desired. Film travel speed may, of course, be made to accurately follow a predetermined speed versus location relationship to provide the desired focal trough shape.

The present invention provides significant reduction in X-ray beam intensity with an accompanying dose reduction to the patient. The present invention device is relatively inexpensive, easy to operate, provides radiographs having good or improved resolution, contrast and shades of grey, and obviates the need for large and expensive image intensifying means and necessary auxiliary electronic equipment for providing full size radiographs, as well as intensifying screens for use with the X-ray film. The lesser amount of power required by the X-ray tubehead enables the size and cost of the tubehead and power supply to be substantially reduced and allows its speed of rotation to be increased resulting in shorter exposure time and less patient motion induced blur.

DETAILED DESCRIPTION OF THE INVENTION

Figure 1:
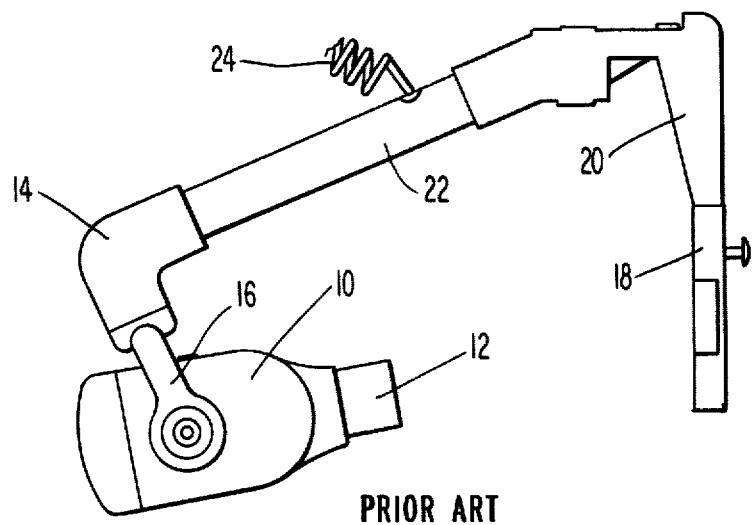
FIG. 1 is an assembly view of a prior art tubehead-camera assembly of a dental X-ray machine.

In FIG. 1 tubehead 10 includes cone 12 which focuses X-rays generated by an X-ray source or tube within the tubehead. Trunnion 14 carries yoke 16 which permits limited tubehead rotation. A camera or film holder assembly 18 contains X-ray film to be activated by the X-ray source. Film holder assembly 18 is supported by a film holder assembly support 20 which receives one end of horizontal arm 22, its other end received by trunnion 14. Horizontal arm 22 and film holder assembly support 20 maintain tubehead 10 and film holder assembly 18 a specified distance from each other and in alignment with the patient's head as tubehead 10 and film holder assembly 18 rotate about the patient. Power is supplied to the X-ray source through cable 24. The entire assembly abovedescribed is supported by an assembly support arm (not shown) which additionally supports a suitable motor (also not shown) for rotating the tubehead and camera assembly as a unit.

Figure 2:
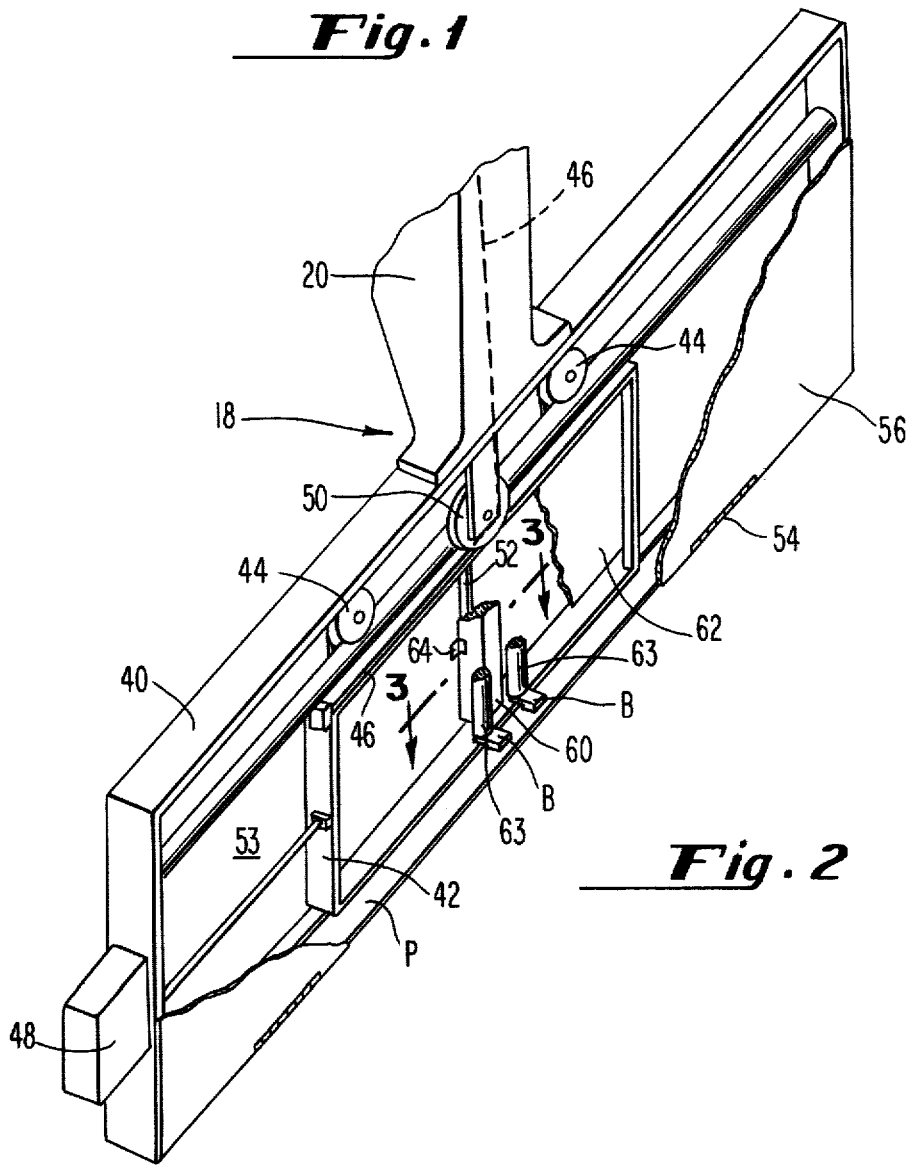
FIG. 2 is a perspective view of the camera (film holder) assembly of FIG. 1 including an image intensifying device positioned for use therewith.

Film holder assembly 18 is conventional, except as modified, later described. It comprises film holder 40 (FIG. 2), film carriage 42 which travels within the film holder along rollers 44 when cable 46 and retrieving spring 48 cooperate, through the cable roller 50 and other means, to move film carriage 42 and its film, modified by elimination of intensifying screens, past vertical slit diaphragm or camera slot 52 disposed centrally the front panel 53 of the film holder assembly. Slit diaphragm 52, of course, permits X-rays from tubehead 10 to pass therethrough for activation of the film. Hinges 54 permit door 56 to be opened for gaining access to the interior of film holder assembly 18. Door 56 is provided with a lead shield (not shown) aligned with tubehead 10 and slot 52.

Cable 46 communicates with suitable structure for controlling the rate of travel of film carriage 42 independently of the speed of rotation of the tubehead-camera assembly. Specific means for controlling rate of film travel speed as well as means for effecting rotation of the tubehead-camera assembly form no part of the present invention. Reference however is again made to the aforementioned U.S. patents and patent application for disclosing and teaching such means.

An image intensifying device 60, light-sensitive film 62, and film guide roller assemblies 63, further modify the structure of conventional film holder assembly 18. Image intensifier 60, in a suitable vacuum envelope, is aligned with slot 52 and is secured thereagainst within the film holder assembly by suitable means, such as brackets 64. The illustrated image intensifier will have nominal dimensions of $5\frac{1}{4}'' \times \frac{1}{2}'' \times \frac{3}{8}''$, the $5\frac{1}{4}'' \times \frac{3}{8}''$ dimension defining an input face which opposes the nominal $5\frac{1}{4}'' \times 17/64''$ opening of slot 52 of the camera.

Figure 3:
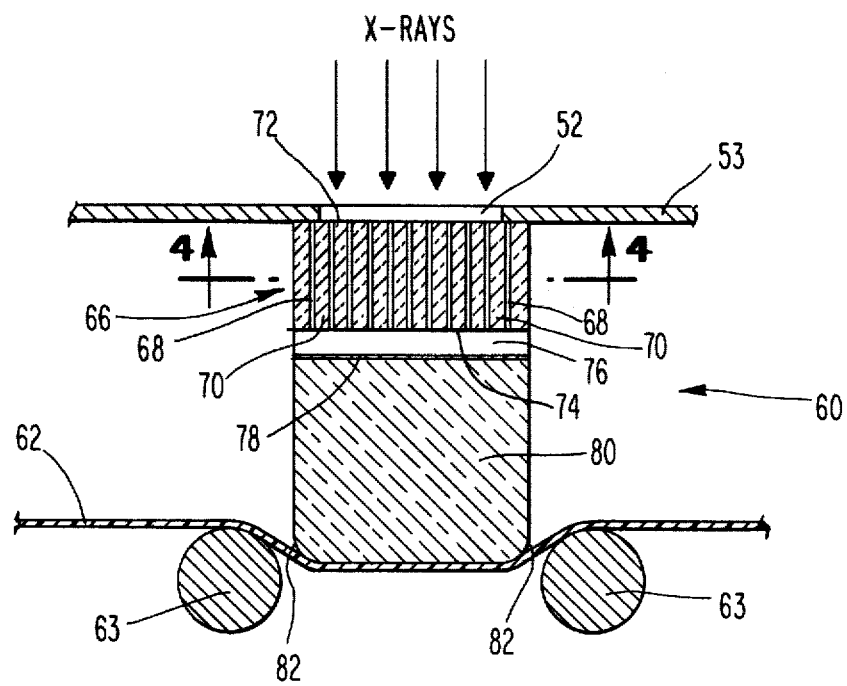
FIG. 3 is a sectional view of the image intensifying device of FIG. 2 taken along line 3—3 thereof.
Figure 4:
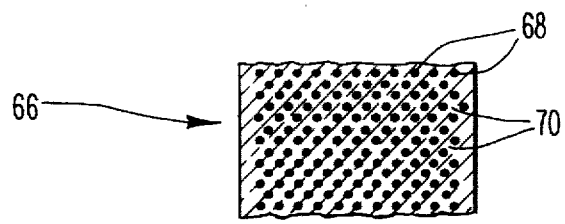
FIG. 4 is a section of the microchannel plate of the image intensifying device of FIG. 3 taken along 4—4 thereof.

The bundles of radiation passing through slot 52 strike the input face of a lead glass microchannel plate 66 (FIGS. 3 and 4) comprising an array of spaced parallel microchannels 68 aligned with the direction of travel of the X-rays. Microchannels 68 are hollow glass cylinders with a known resistive secondary-emission coating disposed on their interior surfaces. Interstices 70, separating the microchannels from each other, comprise a lead glass which converts the X-rays to electrons via bombardment of the lead ions in the glass by the X-rays. The microchannels are electrically connected in parallel by means of a metallic film of chromium disposed on input face 72 and output face 74 of the microchannel plate 66. Alternatively the input face 72 may include a suitable conversion coating or coatings to convert the X-rays to electrons, or the X-rays may be converted to light and the light to electrons. When a potential is applied between these faces by conventional means, an uniform axial electrostatic field is generated in each of the microchannels. Thus, an electron entering a microchannel adjacent the input end of microchannel plate 66 will be vastly multiplied in number before exiting at output face 74 due to cascading action wherein primary electrons, initially formed by the aforementioned bombardment, collide with the secondary-emission coating material to cause secondary electrons to be emitted. These secondary electrons now assume the role of primary electrons for the next collision further down the microchannel, and so on.

A typical gain of $10^3$ electrons is realized by means of microchannel plate 66, although gains in the millions are readily currently achievable. Our laboratory tests suggest that gain values of less than 1000 and probably less than 100 will suffice for the present application. It is appreciated that other image intensifier techniques which will convert the X-rays to electrons, multiply them, and then provide an amplified light output may be used advantageously with the present invention. In some cases, the efficient conversion of the X-rays to light by microchannel plate structures without amplification may also be used advantageously with the present invention.

Typically, microchannel 68 is about 12 microns in diameter. The microchannels have a center-to-center spacing of about 15 microns. Since microchannel plate 66 is approximately ⅛" in thickness, the length-to-diameter ratio of each microchannel is about 250.

The multiplied electrons leaving output face 74 are accelerated by about 5 kV across a gap 76 of about 0.05". The accelerated electrons are caused to impinge on a phosphor screen 78 disposed on the input side of a fiber optic face plate 80. Phosphor screen 78 converts the electrons to light images which are transmitted through fiber optic face plate 80 to thereby activate the fast light-sensitive film 62. Film 62 comprises a single or double emulsion layer having a conventional backing plate, the emulsion layer facing the image intensifier. Intensifying screens used with conventional X-ray equipment, are not used or required in the practice of the present invention.

The resultant intensified image may have static and dynamic resolutions exceeding 10 and 7 line paris/mm respectively. The radiation dosage to the patient is reduced by about 10 to 1. Experiments have confirmed 40 to 1 dosage reductions but with some increase in noise level. Optimum results for any specific applications therefore requires balancing dose reduction and noise. As aforementioned, electron gain, and hence dose reduction, may be achieved by adjusting potential applied to the image intensifier.

Means are known for applying a potential across input face 72 and output face 74 of the microchannel plate; for providing a sufficient voltage across gap 76 to accelerate the multiplied electrons from microchannel plate 66 to phosphor screen 78; and for vacuum sealing the entire image intensifying device 60 for proper operation thereof.

Image intensifier 60 has an indicated depth of about ¼" which may readily be changed by simply increasing or decreasing the depth of fiber optic face plate 80. The nominal ¼" depth of image intensifier 60 is accommodative to the existing film holder assembly 18 without requiring unnecessary modifications thereto. Film guide roller assemblies 63 (FIGS. 2 and 3) permit film 62 to travel unimpeded in constant low pressure contact relationship across the output face of fiber optic face plate 80 in accordance with a rate of speed dictated by the radiographic image desired. Film guide roller assemblies 63 are rotatably mounted on brackets B, secured to bottom plate P of film holder assembly 18. Means for adjusting the film guide roller assemblies in order to accommodate image intensifiers of varying depths are known and are not disclosed or illustrated herein. Although only one roller guide for each film guide roller assembly 63 is shown, it is understood that a pair of cooperating rollers for each such assembly may be used, if desired. Alternatively, the film guide roller assemblies may be mounted to door 56.

Output face of fiber optic face plate 80 is provided with small radii 82 in order to prevent possible damage to film 62 as it lightly slides thereacross. Although film 62 will, ideally, contact the output face of fiber optic face plate 80, light image scatter is within tolerable limits if distance between film 62 and output face of face plate 80 is maintained less than about 0.005".

It is understood of course that the individual fibers comprising fiber optic face plate 80 are aligned in the same direction as microchannels 68.

It is envisaged that certain structures may require a fiber optic face plate of substantially increased depth. The present inventive device may be used therewith since fiber optic face plates permit an image plane to be transmitted directly to its outer surface without the danger of generating internal reflections.

The present invention provides an additional fraction of an inch between the patient's head and camera, that is, the distance between the focal spot of the X-ray tube within tubehead 10 to the X-ray film carried by film carriage 42. Since the input surface of lead glass microchannel plate 66 now becomes the active detecting area, as opposed to the film therebehind, it is possible to move the camera of film holder assembly 18 slightly farther from the patient's head. This feature could be physically and psychologically comforting to patient's with large proboscises, or to patient's having interfering hairstyles. By use of fiber optic face plates of substantial depth, it is thus possible to move the film holder assembly a substantial distance from the image intensifier to provide a less cluttered design.

The invention is not intended to be limited to the image intensifying device shown and described. For example, X-ray detection or image intensifying devices employing scintillators, photocathodes, aluminized phsophor screens, electronic multiplier arrays of various types, etc. may be used advantageously with the present invention, with or without adaptation.

Film holder assembly 18 will be made light tight be conventional means prior to patient radiographing.

An embodiment of the invention constructed in accordance with the principles disclosed herein utilized an X-ray source capable of generating a continuous series of X-ray pulses for producing panoramic radiographs. The X-rays are generated by 50 to 90 kVp applied to a half-wave self-rectified tungsten anode X-ray tube, the incoming X-rays having an input energy ranging between about 20 to 40 keV effective. The sum of the image intensifier, phosphor, etc. rise times and decay times should typically be less than 760 microseconds in order that target system resolution will be obtained. Fast, light-sensitive dental film in the neighborhood of ASA 3000 may be used although slower film, approaching ASA 400 also gave good results. Phosphor screen 78 must be spectrally matched to the film used to insure optimal activation of the film be the light images. The light images emanating from phosphor screen 78 have a spectral radiance wavelength ranging between about 250–425 nanometers.

Panoramic techniques in current use by the assignee of the present invention employ 50 to 90 kVp at 5 mA for about 20 seconds duration. Panoramic techniques employing the principles of the instant invention require only 50 kVp maximum at 0.5 mA for the same duration. The focal spot of the X-ray tube to film 62 distance is 16.84" nominal.

The invention is not intended to be limited to dental radiography, since one skilled in the art may readily adapt the principles disclosed herein, for example, to tomographic medical panoramic apparatus.

I claim:

1. An X-ray machine comprising an X-ray source adapted to continuously direct radiation through a slot disposed in a front panel of a film holder assembly containing film controllably movable therewithin for sequentially exposing portions thereof to radiation passing through a patient disposed between said X-ray source and film holder assembly to form a full size panoramic radiograph, in combination therewith of the improvement thereto comprising image intensifying means secured within said film holder assembly in operable alignment with said slot for converting radiations passing through said patient and said slot to electrons which are multiplied within said means to produce intensified light images, said image intensifying means having an input face substantially equivalent in size to the dimensions of said slot and including light transmitting means for directly transmitting said intensified light images, said film being devoid of intensifying screens normally associated therewith and in direct sliding contact relationship with an output face of said light transmitting means for continuously receiving said intensified light images from said light transmitting means to form radiographic images on said full size panoramic radiograph.

2. The X-ray machine of claim 1 wherein said light transmitting means is a fiber optic face plate.

3. The X-ray machine of claim 2 wherein said film is disposed in near-contacting relationship with said output face of said fiber optic face plate of said image intensifying means.

4. The X-ray machine of claim 3 wherein said near-contacting relationship represents a distance less than about 0.005".

5. In a panoramic dental X-ray machine for providing full size radiographs of dental arch areas of a patient seated in a chair adapted for movement, said X-ray machine comprising a. an X-ray source, and
    b. a film holder assembly for holding film to be activated by said source, said film holder assembly having a slot in a front panel thereof to permit radiation from said X-ray source passing through said dental arch area of said patient to pass therethrough, said X-ray machine including means to power said X-ray source and means for controllably continuously moving said film in said film holder assembly past said slot, and other means for orbiting said X-ray source and film holder assembly about said dental arch area of said patient, the combination therewith of the improvement thereto comprising image intensifying means for converting said radiations passing through said patient and said slot to electrons which are multiplied within said image intensifying means to produce intensified light images, said image intensifying means being secured within said film holder assembly in operable alignment with said slot, said image intensifying means having an input face substantially equivalent in size to the dimensions of said slot and including light transmitting means for continuously receiving and transmitting said intensified light images, said film being devoid of intensifying screens normally associated therewith and in direct sliding contact relationship with an output face of said light transmitting means for continuously receiving said intensified light images on said full size panoramic radiograph.

6. The X-ray machine of claim 5 wherein said light transmitting means is a fiber optic face plate.

7. The X-ray machine of claim 6 wherein said film is disposed in near-contacting relationship with said output face of said fiber optic face plate of said image intensifying means.

8. The X-raymachine of claim 7 wherein said near-contact relationship represents a distance less than about 0.005".

* * * * *